United States Patent [19]

Perronnet et al.

[11] 3,931,175
[45] Jan. 6, 1976

[54] IMIDAZO(1,2B)PYRIDAZINYL ESTERS, PROCESS AND INSECTICIDAL COMPOSITIONS

[75] Inventors: Jacques Perronnet, Paris; Laurent Taliani, Les Pavillons-sous-Bois, both of France

[73] Assignee: Roussel-UCLAF, Paris, France

[22] Filed: July 1, 1974

[21] Appl. No.: 484,774

[30] Foreign Application Priority Data
July 5, 1973 France .............................. 73.24736

[52] U.S. Cl. ...... 260/250 AC; 424/250; 260/250 AP
[51] Int. Cl.² ....................................... C07D 237/26
[58] Field of Search ............... 260/250 AC, 250 AP

[56] References Cited
UNITED STATES PATENTS

| | | | |
|---|---|---|---|
| 3,100,206 | 8/1963 | Rigterink | 260/250 AP |
| 3,808,227 | 4/1974 | Hoffmann et al. | 260/310 R |
| 3,878,210 | 4/1975 | Lorenz et al. | 260/250 AP |

Primary Examiner—Richard J. Gallagher
Assistant Examiner—Anne Marie T. Tighe
Attorney, Agent, or Firm—Hammond & Littell

[57] ABSTRACT

Substituted imidazo(1,2b)pyridazinyl esters having the formula

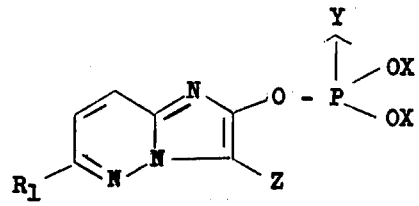

wherein $R_1$ is hydrogen or halogen, Y is oxygen or sulfur, X is alkyl having 1 to 6 carbon atoms and Z is hydrogen or —COOR' wherein R, is alkyl having 1 to 6 carbon atoms; as well as the process of preparation, insecticidal compositions containing the same, and the method of using the insecticidal compositions. The products of the invention are useful in agriculture to combat and control insects.

9 Claims, No Drawings

IMIDAZO(1,2B)PYRIDAZINYL ESTERS, PROCESS AND INSECTICIDAL COMPOSITIONS

OBJECTS OF THE INVENTION

An object of the present invention is the development of substituted imidazo(1,2b)pyridazinyl esters having the formula

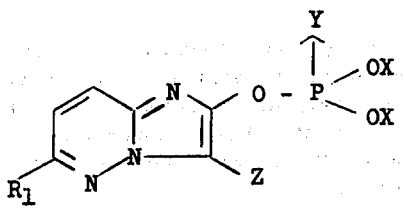

wherein $R_1$ is a member selected from the group consisting of hydrogen and halogen, Y is a member selected from the group consisting of oxygen and sulfur, X is alkyl having 1 to 6 carbon atoms, and Z is a member selected from the group consisting of hydrogen and —COOR', wherein R' is alkyl having 1 to 6 carbon atoms.

Another object of the present invention is the development of a process for the production of the above substituted imidazo(1,2b)pyridazinyl esters consisting essentially of the steps of reacting a chlorophosphate having the formula

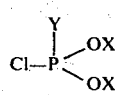

wherein Y is a member selected from the group consisting of oxygen and sulfur and X is alkyl having 1 to 6 carbon atoms with a reactant selected from the group consisting of a. an alkali metal alcoholate having the formula

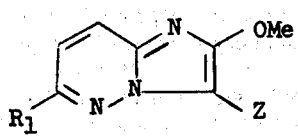

wherein $R_1$ is a member selected from the group consisting of hydrogen and halogen, Z is a member selected from the group consisting of hydrogen and —COOR', wherein R' is alkyl having 1 to 6 carbon atoms, and Me is an alkali metal, and b. an alcohol having the formula

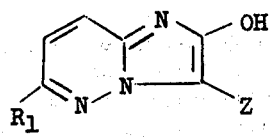

wherein $R_1$ and Z have the above-assigned values in the presence of a tertiary organic base, in the presence of an inert organic solvent, and recovering said substituted imidazo(1,2b)pyridazinyl esters.

A yet further object of the present invention is the development of insecticidal compositions containing said substituted imidazo(1,2)pyridazinyl esters and the method of combatting insects employing said esters.

These and other objects of the present invention will become more apparent as the description thereof proceeds.

DESCRIPTION OF THE INVENTION

We have now discovered new substituted imidazo(1,2b)pyridazines of formula I

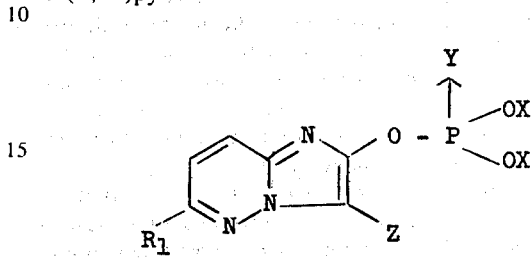

in which $R_1$ represents an atom of hydrogen or halogen, Y represents an atom of oxygen or sulfur, X represents an alkyl having 1 to 6 carbon atoms, and Z represents either an atom of hydrogen, or a —COOR' group in which R' represents an alkyl having 1 to 6 carbon atoms. In particular, the invention concerns the products of formula I in which $R_1$ represents an atom of halogen, preferably chlorine. However, the invention equally concerns the products of formula I in which $R_1$ represents an atom of hydrogen.

Among the products of formula I are particularly those described in the examples, specifically:

a. 2-(dimethoxythiophosphoryloxy)-6-chloro-imidazo(1,2b)-pyridazine
b. 2-(diethoxythiophosphoryloxy)-6-chloro-imidazo(1,2b)-pyridazine
c. 2-(diethoxythiophosphoryloxy)-3-carbethoxy-6-chloro-imidazo(1,2b)pyridazine
d. 2-(diethoxythiophosphoryloxy)-imidazo(1,2b)pyridazine
e. 2-(dimethoxyphosphoryloxy)-imidazo(1,2b)pyridazine.

The new substituted imidazo(1,2b)pyridazines of formula I are endowed with remarkable insecticidal properties which makes them useful in agriculture in combatting and controlling insects.

The insecticidal properties of the products of formula I have been demonstrated by tests on the various insects: Blabera Fusca, Blattella Germanica, Sitophilus Granarius, Musca Domestica (adults or larvae), Aphis Fabae, Noctuae, Ceratitis Capitata. Examples of these tests are given in the following text.

The invention also relates to the process for the preparation of the products of formula I. This process is characterized in that a 2-hydroxy-6-$R_1$-imidazo(1,2b)-pyridazine of formula II

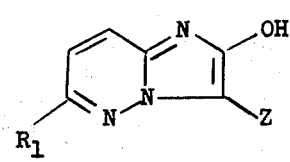

II or an alkali metal salt thereof, is reacted with 0,0-dialkylchlorophosphate or chlorothiophosphate of formula III

where, in the formulas, $R_1$, X, Y and Z have the meanings already indicated, while effecting this reaction in the presence of a tertiary base when the 2-hydroxylated derivative of formula II is the starting material.

The condensation of the chlorophosphate or chlorothiophosphate of formula III with the hydroxylated derivative of formula II or its alkali metal salt is advantageously carried out in the presence of an inert organic solvent such as, for example, tetrahydrofuran, dimethylformamide or acetonitrile.

More particularly, the process of the invention involves the production of the above-described substituted imidazo(1,2b)pyridazines or substituted imidazo(1,2b)-pyridazinyl esters consisting essentially of the steps of reacting a chlorophosphate having the formula

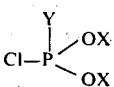

wherein Y is a member selected from the group consisting of oxygen and sulfur and X is alkyl having 1 to 6 carbon atoms with a reactant selected from the group consisting of a. an alkali metal alcoholate having the formula

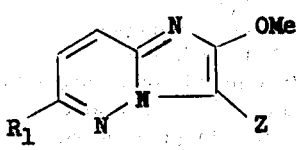

wherein $R_1$ is a member selected from the group consisting of hydrogen and halogen, Z is a member selected from the group consisting of hydrogen and —COOR', wherein R' is alkyl having 1 to 6 carbon atoms, and Me is an alkali metal, and b. an alcohol having the formula

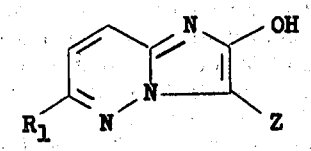

wherein $R_1$ and Z have the above-assigned values in the presence of a tertiary organic base, in the presence of an inert organic solvent, and recovering said substituted imidazo(1,2b)pyridazinyl esters.

Further, the invention relates to a process for the preparation of products of formula I, in which $R_1$ represents an atom of halogen, especially chlorine, characterized in that a 2-hydroxy-6-R-imidazo(1,2b)pyridazine of the formula

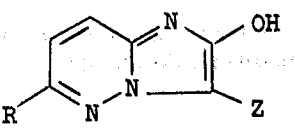

in which R represents an atom of halogen and Z has the above-recited meaning, is reacted, in the presence of a tertiary base, with an 0,0-dialkyl chlorophosphate or chlorothiophosphate of the formula

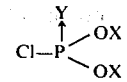

in which X and Y have the already indicated meanings.

In addition, the invention relates to a process for the production of products of formula I, in which $R_1$ represents an atom of hydrogen, characterized in that an alkali metal salt of 2-hydroxy-imidazo(1,2b)pyridazine of the formula

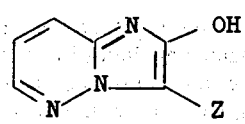

is reacted with an 0,0-dialkyl chlorophosphate or chlorothiophosphate of the formula

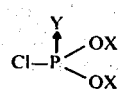

in which formulas X, Y and Z have the previously indicated meanings.

The tertiary base employed in the condensation of the chlorophosphate or chlorothiophosphate with the hydroxylated derivative, can be a tertiary amine base, such as trilower alkylamine, for example, triethylamine or an aromatic tertiary amine, for example, pyridine.

The process of preparation of the starting compound 6-chloro-2-hydroxy-imidazo(1,2b)pyridazine (II, $R_1$ = Cl and Z = H) is described by Ostroversnick in Croatica Chemica Acta, 41, 135 (1969). The other 2-hydroxy-6-$R_1$-imidazo(1,2b)pyridazines can be prepared by analogous processes. The process for the preparation of 2-hydroxy-3-carbethoxy-6-chloroimidazo(1,2b)pyridazine (II, $R_1$ = Cl and Z = $COOC_2H_5$) and of the potassium salt of 2-hydroxy-imidazo(1,2b)pyridazine (II, $R_1$ and Z = H) is described in the examples. The other 2-hydroxy-3-carbalkoxy-6-$R_1$-imidazo(1,2b)pyridazines can be prepared by analogous processes.

The 0,0-dialkyl chlorothiophosphates can be prepared by the reaction of $PSCl_3$ with the corresponding alcohol. The 0,0-dialkyl chlorophosphates can be prepared by the reaction of $POCl_3$ with the corresponding alcohol.

The invention also relates to insecticidal compositions containing, as active material, an insecticidally effective amount of at least one product of formula I and, optionally, further containing one or several other pesticidal agents. The insecticidal compositions may be in the form of powders, granules, suspensions, emulsions, solutions and solutions for aerosols.

In addition to the active product, the insecticidal compositions generally contain a vehicle and/or a cationic, anionic or non-ionic surface-active compound to assure a uniform distribution of the active material in the insecticidal composition and in its final application form. The vehicle may be a liquid such as water, alcohol, hydrocarbons or other organic solvents, or a mineral, animal or vegetable oil; or an inert powder such as talc, clays, silicates, or Kieselguhr. Preferably the insecticidal compositions contain from 0.2 to 90% by weight of at least one compound of formula I.

An example of a suitable insecticidal composition is an emulsifiable concentrate containing, by weight, 25% of 2-(diethoxythiophosphoryloxy)-6-chloro-imidazo(1,2b)-pyridazine, 6.4% of "Altox 4851", 3.2% of "Altox 4855" and 65.4% of xylene. "Altox 4851" is the tradename for a mixture of an alkylaryl sulfonate and polyoxyethylenated triglycerides having a viscosity of 300 to 700 cps at 20°C. Altox 4855 is the tradename for a mixture of an alkylaryl sulfonate and polyoxyethylenated triglycerides having a viscosity of 1500 to 1900 cps at 25°C.

The compositions have interesting insecticidal activity in domestic and agricultural fields for the control of insect pests at low concentrations. The liquid or powders designed for application to foliage, preferably contain from 10 to 80% by weight of at least one product of formula I. The powders or liquids for treatment of grains and seeds contain preferably from 0.5 to 90% by weight of at least one product of formula I.

The novel method for combatting and controlling insects comprises contacting insects with an insecticidally effective amount of at least one compound of formula I.

The following examples are illustrative of the invention without being limitative in any respect.

EXAMPLE 1

2-(dimethoxythiophosphoryloxy)-6-chloro-imidazo(1,2b)pyridazine 34 gm of 2-hydroxy-6-chloro-imidazo(1,2b)pyridazine, 20.5 gm of triethylamine and 32 gm of O,O-dimethyl chlorothiophosphate were introduced into 500 cc of tetrahydrofuran. The mixture was agitated for 15 hours. The triethylamine hydrochloride formed was eliminated by filtration and the filtrate was concentrated to dryness. The residue obtained was dissolved in a mixture composed of 3 volumes of ethyl acetate and 7 volumes of cyclohexane. The solution obtained was filtered through silica gel. The filtrate thus obtained was concentrated to dryness. The residue was triturated with petroleum ether (b.p. 65° to 75°C) and crystallized from isopropyl ether. 23 gm of 2-(dimethoxythiophosphoryloxy)-6-chloro-imidazo(1,2b)-pyridazine was obtained melting at 88°C.

Analysis: $C_8H_9ClN_3O_3PS$: Calculated: 32.73% C; 3.09% H; 12.07% Cl; 14.30% N; 10.55% P. Found: 32.9% C; 3.2% H; 12.1% Cl; 14.4% N; 10.6% P.

EXAMPLE 2

2-(diethoxythiophosphoryloxy)-6-chloro-imidazo(1,2b)pyridazine 19 gm of 2-hydroxy-6-chloro-imidazo(1,2b)-pyridazine and 21 gm of O,O-diethyl chlorothiophosphate were introduced into a mixture of 11.3 gm of triethylamine and 125 cc of dimethylformamide. The mixture was allowed to stand for 2 hours and 30 minutes at room temperature. Then water and ice were added and the mixture was extracted with ethyl ether. The organic phase was dried and concentrated to dryness. The residue was triturated with petroleum ether (b.p. 65° to 75°C) and the crystals formed were separated by vacuum filtration. These crystals were dissolved in a mixture of cyclohexane and ethyl acetate (1 to 1) and subjected to chromatography through silica gel. The eluant was concentrated to dryness. The crystals obtained were triturated with petroleum ether (b.p. 65° to 75°C) and, in two lots, 22 gm of 2-(diethoxythiophosphoryloxy)-6-chloro-imidazo(1,2b)pyridazine were obtained having a melting point of 59°C.

Analysis: $C_{10}H_{13}ClN_3O_3PS$: Calculated: 37.35% C; 4.07% H; 11.02% Cl; 13.06% N; 9.62% P. Found: 37.2% C; 4.3% H; 11.2% Cl; 13.2% N; 9.7% P.

EXAMPLE 3

2-(diethoxythiophosphoryloxy)-3-carbethoxy-6-chloroimidazo(1,2b)pyridazine

Step A: 2-Hydroxy-3-Carbethoxy-6-Chloro-Imidazo(1,2b)pyridazine 52 gm of 3-amino-6-chloro-pyridazine and 48 gm of diethyl bromoalonate were introduced into 260 cc of dimethylformamide. The mixture was heated to 130°C for 10 minutes and then poured over ice. The precipitate formed was isolated by vacuum filtration, washed with water, with acetone and dried. 29 gm of 2-hydroxy-3-carbethoxy-6-chloro-imidazo(1,2b)pyridazine were obtained melting at 200°C.

After recrystallization from acetic acid, the melting point remained unchanged at 200°C.

Analysis: $C_9H_8ClN_3O_3$: Calculated: 44.74% C; 3.33% H; 17.39% N; 14.67% Cl. Found: 44.4% C; 3.2% H; 17.5% N; 14.7% Cl.

Step B: 2-(Diethoxythiophosphoryloxy)-3-Carbethoxy-6-Chloro-Imidazo(1,2b)Pyridazine 12 gm of 2-hydroxy-3-carbethoxy-6-chloro-imidazo-(1,2b)pyridazine, 5 gm of triethylamine and 9.5 gm of O,O-diethyl chlorothiophosphate was introduced into 50 cc of dimethylformamide. The mixture was agitated for 3 hours, poured into water, and extracted with ethyl ether. The extract was dried and concentrated to dryness. The residue was subjected to chromatography through silica gel with elution with a mixture of cyclohexane and ethyl acetate (6 to 4).

After concentration and separation of the crystals, 14 gm of 2-(diethoxythiophosphoryloxy)-3-carbethoxy-6-chloro-imidazo(1,2b)pyridazine were obtained, melting at 78°C.

Analysis: $C_{13}H_{17}ClN_3O_5PS$:

Calculated: 39.65% C; 4.35% H; 10.67% N; 9.01% Cl; 7.85% P.

Found: 39.5% C; 4.4% H; 10.6% N; 8.9% Cl; 7.8% P.

EXAMPLE 4

2-(diethoxythiophosphoryloxy)-imidazo(1,2b)-pyridazine 15 gm of the potassium salt of 2-hydroxyimidazo(1,2b)pyridazine, 250 cc of acetonitrile and 17 gm of O,O-diethyl chlorothiophosphate were mixed and agitated for 20 hours at room temperature. The mixture was then filtered and the filtrate was evaporated to dryness. The residue was subjected to chromatography through silica gel with elution with a 1-to-1 mixture of cyclohexane and ethyl acetate. After evaporating the solvent, 17 gm of 2-(diethoxythiophosphoryloxy)-imidazo (1,2b)pyridazine were obtained in the form of an oil, $n_D^{20} = 1.5647$.

Analysis: $C_{10}H_{14}N_3O_3PS$:

Calculated: 41.81% C; 4.91% H; 14.62% N; 10.78% P.

Found: 41.5% C; 5.1% H; 14.5% N; 10.4% P.

The starting material, the potassium salt of 2-hydroxy-imidazo(1,2b)pyridazine, was prepared as follows:

51 gm of 2-hydroxy-6-chloro-imidazo(1,2b)pyridazine were mixed with 42 gm of potassium methylate, 500 cc of methanol and 6 gm of palladized charcoal containing 10% of palladium. The mixture was agitated in a hydrogen atmosphere at room temperature until absorption of the theoretical amount of hydrogen occurred. The mixture was then filtered and the filtrate was evaporated.

50 gm of the potassium salt of 2-hydroxy-imidazo(1,2b)pyridazine in the form of a brown solid were obtained.

EXAMPLE 5

2-(dimethoxyphosphoryloxy)-imidazo(1,2b)pyridazine 19 gm of the potassium salt of 2-hydroxy-imidazo(1,2b)pyridazine were mixed with 180 cc of acetonitrile and 14.5 gm of 0,0-dimethyl chlorophosphate. The mixture was agitated overnight at room temperature and then filtered. The filtrate was evaporated to dryness. The residue was subjected to chromatography through silica gel with elution with a 1-to-1 mixture of acetone and chloroform. After evaporation, an oil was thus obtained which crystallized slowly. The crystals obtained were washed with ethyl ether and vacuum filtered. 9.5 gm of 2-(dimethoxyphosphoryloxy)imidazo(1,2b)pyridazine were thus obtained, melting at 50° to 52°C.

Analysis: $C_8H_{10}N_3O_4P$:

Calculated: 39.51% C; 4.15% H; 17.28% N; 12.74% P.

Found: 39.2% C; 4.2% H; 17.5% N; 12.4% P.

EXAMPLE 6

Study of the Insecticidal Properties

The following studies were conducted with the compound 2-(diethoxythiophosphoryloxy)-6-chloro-imidazo-(1,2b)pyridazine called hereafter compound A. Similar results can be obtained with any of the other compounds of formula 1.

A. Test on Blatella Germanica

This test was effected by topical application. Adult males of *Blattella Germanica* chosen based on their length, received two microliters of an acetonic solution of the product being tested between the second and third pair of legs. After the treatment, the "test insects" were held in a dim light at 20°C and fed. The mortality was determined after 24 hours, 48 hours and then 5 days after the treatment.

The experimental results for compound A, expressed as a percentage of mortality at given dosages are given in Table I.

TABLE I

| Time | Concentration in ppm | | |
|---|---|---|---|
| | 1250 | 625 | 312 |
| | % Mortality | | |
| 24 hours | 100 | 95 | 65 |
| 48 hours | 100 | 100 | 65 |
| 5 days | 100 | 100 | 60 |

B. Test on *Blabera Fusca* (larva)

The principals of the test were the same as that for *Blatella germanica*, but larvae of *Blabera fusca* of 1.5 to 2 cm of length were employed instead.

Table II gives the experimental results for compound A, as a percent of mortality.

TABLE II

| Time | Concentration in ppm | |
|---|---|---|
| | 5000 | 1250 |
| | % Mortality | |
| 24 hours | 100 | 47 |
| 48 hours | 100 | 53 |
| 5 days | 100 | 53 |

C. Test on *Sitophilus Granarius*

This test was effected by topic application. Acetonic solutions of compound A were prepared corresponding to 5000 mg and 500 mg of active material per liter. 0.2 μ1 of the acetonic solution of compound A were placed on the ventral thorax of the test *Sitophilus granarius*. The test was made on 50 individuals for each concentration. The number of individuals remaining alive and those dead were counted at different intervals of time.

The activity of compound A as expressed as a percent of morality is given in Table III.

TABLE III

| Time | Concentration in ppm | |
|---|---|---|
| | 5000 | 500 |
| | % Mortality | |
| 4 hours | 100 | 57 |
| 24 hours | 100 | 100 |
| 5 days | 100 | 100 |

D. Test on *Musca Domestica*

This test was effected by topic application. The flies received 1 microliter of an acetonic solution of the product tested on the dorsal thorax after having been put to sleep with ether. The insects were then held at 20°C and 50% relative humidity. They were fed with milk or with water. The morality was determined 1 hour, then 24 hours after the treatment.

The experimental results for component A, expressed as a percentage of mortality, are given in Table IV.

TABLE IV

| Time | Concentration in ppm | | | |
|---|---|---|---|---|
| | 5000 | 2500 | 500 | 100 |
| | % Mortality | | | |
| 1 hour | 100 | 100 | 100 | 31 |
| 24 hours | 100 | 100 | 100 | 96 |

E. Test on *Aphis Fabae*

This test was effected by contact-ingestion on bean plants (*Vicia faba*). After spraying 4 cc of solution of the product to be tested, which gives a complete wetting of the plant, the plants were infested by placing on each bean plant 20 wingless adult individuals. The bean plants were then wrapped with gauze in order to hinder the escape of the aphids. Thereafter the living and dead aphids were counted as a function of time. The results were expressed as a percent of Abbott efficacy (corrected according to the Abbott formula in order to eliminate natural mortality).

The results with respect to compound A are given in Table V.

TABLE V

| Time | Concentration in ppm | |
|---|---|---|
| | 100 | 10 |
| | % Abbott efficacy | |
| 2 hours | 95 | 0 |
| 24 hours | 98 | 48 |
| 48 hours | 100 | 100 |

F. Test on Night Moths (*Spodoptera Littoralis*)

This test was made on caterpillars of *Spodoptera littoralis* of 1 to 1.5 cm, aged on the average of 10 days. The test was made by ingestion, 4 cc of an acetonic solution of the product being tested was applied to pieces of lettuce of about 8 mm in diameter which were then placed in closed plastic boxes having a diameter of 5 cm. Fifteen caterpillars wer employed in each treatment.

The caterpillars were held at 20°C and 50% relative humidity and were fed when they ingested the pellets of treated lettuce. The percent mortality was determined 1 hour, 24 hours and 48 hours after treatment.

The experimental results for compound A as expressed as a percent of mortality are given in Table VI.

TABLE VI

| Time | Concentration in ppm | | |
|---|---|---|---|
| | 500 | 250 | 125 |
| | % Mortality | | |
| 1 hour | 10 | 0 | 0 |
| 24 hours | 100 | 60 | 40 |
| 48 hours | 100 | 100 | 100 |

G. Test on larvae of the Domestic Fly (*Musca Domestica*)

This test was effected by contact-ingestion. It consisted in placing 2 cc of an acetonic solution of different concentrations of the product being tested on 1gm of bran, placed on a watch glass. The solvent was allowed to evaporate, then the treated bran was placed in a plastic box. 2 cc of milk were added and, after mixing, the bran was contaminated with 20 larvae of domestic flies, aged 3 to 4 days.

Three repeated tests were made for each concentration. The larvae were held at 20°C and 30% relative humidity. The percent morality was determined 48 hours and 8 days after treatment.

The results for compound A, expressed as percent mortality, are given in Table VII.

TABLE VII

| Time | Concentration in ppm | | |
|---|---|---|---|
| | 5000 | 500 | 50 |
| | % Mortality | | |
| 48 hours | 100 | 78 | 75 |
| 8 days | 100 | 89 | 67 |

H. Test on *Ceratitis Capitata*

This test was effected by topic application. Acetonic solutions of compound A were prepared corresponding to 1000 mg, 100 mg and 10 mg of active material per liter. 1 µl of the acetonic solutions of compound A was placed on the dorsal thorax of *Ceratitis Capitata* flies aged 2 to 3 days. The test was made on fifty individuals at each concentration. The number of living flies and those dead were counted at different intervals of time.

The activity of compound A, as expressed as percent mortality, is given in Table VIII.

TABLE VIII

| mg of Compound A/l or Nanogram/insect | % Mortality | |
|---|---|---|
| | 2 hours | 24 hours |
| 1000 | 100 | 100 |
| 100 | 98 | 100 |
| 10 | 37.2 | 68.6 |

I. Conclusions

The different tests utilized demonstrate the interesting insecticidal properties of 2-(diethoxythiophosphoryloxy)-6-chloro-imidazo(1,2b)pyridazine (compound A). As indicated, the other compounds of formula I have comparable insecticidal properties.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. Substituted imidazo(1,2b)pyridazinyl esters having the formula

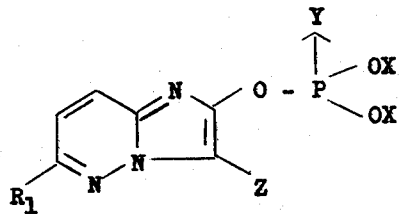

wherein $R_1$ is a member selected from the group consisting of hydrogen and halogen, Y is a member selected from the group consisting of oxygen and sulfur, X is alkyl having 1 to 6 carbon atoms, and Z is a member selected from the group consisting of hydrogen and —COOR', wherein R' is alkyl having 1 to 6 carbon atoms.

2. The substituted imidazo(1,2b)pyridazinyl esters of claim 1 wherein $R_1$ is halogen.

3. The substituted imidazo(1,2b)pyridazinyl esters of claim 1 wherein $R_1$ is hydrogen.

4. The substituted imidazo(1,2b)pyridazinyl esters of claim 1 wherein said ester is 2-(dimethoxythiophosphoryloxy)-6-chloro-imidazo(1,2b)pyridazine.

5. The substituted imidazo(1,2b)pyridazinyl esters of claim 1 wherein said ester is 2-(diethoxythiophosphoryloxy)-6-chloro-imidazo(1,2b)pyridazine.

6. The substituted imidazo(1,2b)pyridazinyl esters of claim 1 wherein said ester is 2-(diethoxythiophosphoryloxy)-3-carbethoxy-6-chloro-imidazo(1,2b)-pyridazine.

7. The substituted imidazo(1,2b)pyridazinyl esters of claim 1 wherein said ester is 2-(diethoxythiophosphoryloxy)-imidazo(1,2b)pyridazine.

8. The substituted imidazo(1,2b)pyridazinyl esters of claim 1 wherein said ester is 2-(dimethoxyphosphoryloxy)-imidazo(1,2b)pyridazine.

9. A compound of claim 1 wherein $R_1$ is hydrogen or chlorine.

* * * * *